United States Patent
De Vos et al.

(10) Patent No.: US 9,353,175 B2
(45) Date of Patent: May 31, 2016

(54) USE OF ANTAGONISTS TARGETING METALLOTHIONEIN TO TREAT INTESTINAL INFLAMMATION

(71) Applicants: UNIVERSITEIT GENT, Ghent (BE); UNIVERSITY OF CONNECTICUT, Farmington, CT (US)

(72) Inventors: Martine De Vos, De Pinte (BE); Debby Laukens, Brecht (BE); Lindsey DeVisscher, Moortsele (BE); Michael A. Lynes, Eastford, CT (US)

(73) Assignees: UNIVERSITEIT GENT, Ghent (BE); UNIVERSITY OF CONNECTICUT, Farmington, CT (US)

( * ) Notice: Subject to any disclaimer, the term of this patent is extended or adjusted under 35 U.S.C. 154(b) by 0 days.

(21) Appl. No.: 14/581,465

(22) Filed: Dec. 23, 2014

(65) Prior Publication Data

US 2015/0158940 A1 Jun. 11, 2015

Related U.S. Application Data

(63) Continuation of application No. 14/131,406, filed as application No. PCT/EP2012/063372 on Jul. 9, 2012, now abandoned.

(30) Foreign Application Priority Data

Jul. 8, 2011 (EP) .................................... 11173275

(51) Int. Cl.
| | | |
|---|---|---|
| *A61K 39/395* | (2006.01) | |
| *C07K 16/18* | (2006.01) | |
| *A01K 67/027* | (2006.01) | |
| *C07K 14/825* | (2006.01) | |
| *A61K 39/00* | (2006.01) | |

(52) U.S. Cl.
CPC ............. *C07K 16/18* (2013.01); *A01K 67/0275* (2013.01); *A01K 67/0276* (2013.01); *C07K 14/825* (2013.01); *A01K 2217/052* (2013.01); *A01K 2217/075* (2013.01); *A01K 2227/105* (2013.01); *A01K 2267/0368* (2013.01); *A61K 2039/505* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | |
|---|---|---|
| 2003/0007973 A1 | 1/2003 | Lynes |
| 2007/0071675 A1* | 3/2007 | Wu ....................... C07K 16/245 424/1.49 |

OTHER PUBLICATIONS

Devisscher et al., J Pathol 2014; 233: 89-100.*
John C. Barbato et al., "Arteriosclerosis, Thrombosis, and Vascular Biology", Journal of the American Heart Association, Arterioscler. Throm. Vasc. Biol. 2007, Nov. 2, 2006, pp. 49-54.
Daniel Burger et al., "Conventional Medical Management of Inflammatory Bowel Disease", Gastroenterology 2011, pp. 1827-1837.e2.
Michael A. Lynes et al., "Immunomodulatory activities of extracellular metallothionein I. Metallothionein effects on antibody production", Toxicology 85 (1993), pp. 161-177.
Scott E. Plevy et al., "Future Therapeutic Approaches for Inflammatory Bowel Diseases", Gastroenterology 2011, pp. 1838-1846.
Prasad N. Paradkar et al., "Dietary isoflavones suppress endotoxin-induced inflammatory reaction in liver and intestine", Cancer Letters 215 (2004), p. 21-28.
C.D. Tran et al., "The Role of Zinc ad Metallothionein in the Dextran Sulfate Sodium-Induced Colitis Mouse Model", Dig. Dis. Sci. (2007), vol. 52, pp. 2113-2121.
Anouk Waeytens, et al., "Evidence for a Potential Role of Metallothioneins in Inflammatory Bowel Diseases", Mediators of Inflammation, vol. 2009, Article ID 729172, pp. 1-9.
James T. Wu, "Circulating Homocysteine Is an Inflammation Marker and a Risk Factor of Life-Threatening Inflammatory Diseases", J. Biomed. Lab. Sci. 2007, vol. 19, No. 4, pp. 107-112.
S. Helieh et al., "Metallothionein overexpression does not protect against inflammatory bowel disease in a murine colitis model", Med Sci. Monit., 2005, pp. 1-6.

* cited by examiner

*Primary Examiner* — Marianne P Allen

(57) ABSTRACT

Metallothioneins are stress inducible proteins with modulating functions during inflammation. Antagonizing metallothioneins during gut inflammation reduces markers of inflammations and enhances recuperation of intestinal inflammation.

6 Claims, 9 Drawing Sheets

USE OF ANTAGONISTS TARGETING METALLOTHIONEIN TO TREAT INTESTINAL INFLAMMATION

CROSS-REFERENCE TO RELATED APPLICATION

This application is a continuation of Ser. No. 14/131,406, filed Jan. 7, 2014 which was filed under 35 U.S.C. 371 as a U.S. national phase application of PCT/EP2012/063372, having an international filing date of Jul. 9, 2012, which claims the benefit of European Patent Application No. 11173275.6, having a filing date of Jul. 8, 2011, all of which are hereby incorporated by reference.

TECHNICAL FIELD OF INVENTION

The present invention is based on the finding that reducing bioactive metallothionein levels during intestinal inflammation results in a significant therapeutic effect. Hence, the present invention relates to antagonists targeting metallothionein, such as anti-metallothionein antibodies, and provides new therapeutics for the treatment of intestinal inflammation such as inflammatory bowel diseases.

BACKGROUND ART

Inflammatory bowel diseases (IBD) comprising Crohn's disease and ulcerative colitis are inflammatory conditions of the colon and/or the small intestine. Symptoms may overlap with other forms of chronic intestinal inflammatory conditions such as collagenous-, lymphocytic-, ischemic-, diversion- and indeterminate colitis and Behçet's disease. The exact etiology of these diseases is believed to be multifactorial but is to date still undefined (Gastroenterology, Vol 150, No 6 May 2011, 1701-1846). Therefore, current treatment aims at dampening the ongoing inflammation and is based on symptoms and presence of lesions. It is clear that new and efficient therapies for IBD with a minimum of side effects are of great interest.

Metallothioneins are cysteine rich zinc binding proteins which play a role in different cellular processes such as zinc homeostasis, oxygen radical scavenging, cell proliferation and apoptosis. They are considered to be acute phase proteins due to their rapid induction by different stimuli, including inflammation (Inoue et al. 2009).

M. Lynes (US 2003/0007973) indicated that an anti-metallothionein antibody is particularly useful to stimulate the immune response in a subject undergoing irradiation or chemotherapy, autoimmune subjects, subjects exposed to immunosuppressive agents, neonates and subjects having undergone transplantation.

Waeytens et al. (2009) review the role of metallothioneins in IBD and conclude that there is a deviant metallothionein expression in IBD but that the role of these proteins during disease is not clear.

Tran et al. (2007) and Oz et al. (2005) investigated the effect of the presence or absence of metallothioneins via metallothionein knock-out mice but could not observe a significant and beneficial effect of the absence of metallothioneins.

Devisscher et al. (2011; abstract) describe that metallothioneins have been proposed to have a role in the pathogenesis of IBD and conclude that the low metallothionein profile in IBD patients may point to a hypoxia-driven adaptive response in the course of gut inflammation.

Taken together, it remains unclear whether a reduction of metallothionein might have a beneficial role during IBD. The aberrant expression levels in IBD patients and their upregulation during inflammation (De et al. 1990; Laukens et al. 2009)), even suggest a protective effect of metallothionein during intestinal inflammation. The present invention surprisingly demonstrates that administration of antagonists targeting metallothionein, even targeting solely secreted metallothioneins by use of antibodies, results in a significant therapeutic effect of intestinal inflammation.

SUMMARY OF THE INVENTION

The inventors have unexpectedly found that a lack of MTs is beneficial in experimental colitis. Moreover, treatment with an anti-MT antibody reduces the chemotactic properties of extracellular MT, resulting in reduced leukocyte infiltration and dampening of the inflammatory response during colitis and avoids some or all of the negative side effects of other biologic treatments currently used for IBD Hence, anti-MT is an attractive novel biological in the treatment of IBD patients.

The invention therefore provides an antagonist targeting metallothionein for use in treating intestinal inflammation wherein said antagonist is an anti-metallothionein antibody or a fragment thereof which specifically binds to said metallothionein.

In a preferred embodiment, said intestinal inflammation is selected from the group comprising or consisting of: Crohn's disease, ulcerative colitis, collagenous-, lymphocytic-, ischemic-, diversion- and indeterminate colitis and Behçet's disease in mammals.

In another preferred embodiment, said antibody is a monoclonal anti-metallothionein antibody. More preferably, said monoclonal anti-metallothionein antibody is the monoclonal anti-metallothionein antibody clone UC1MT.

The invention further provides a method of treating intestinal inflammation in a subject, comprising the steps of administering to said subject a therapeutically-effective amount of a composition comprising an antibody or a fragment thereof which specifically binds to metallothioneins.

In a preferred embodiment of said method, said antagonist is an anti-metallothionein antibody or a fragment thereof which specifically binds to said metallothionein.

In a preferred embodiment of said method, said intestinal inflammation is selected from the group comprising or consisting of: Crohn's disease, ulcerative colitis, collagenous-, lymphocytic-, ischemic-, diversion- and indeterminate colitis and Behçet's disease in mammals.

In another preferred embodiment of said method, said antibody is a monoclonal anti-metallothionein antibody. More preferably, said monoclonal anti-metallothionein antibody is the monoclonal anti-metallothionein antibody clone UC1MT.

DESCRIPTION OF INVENTION

Figure 1:
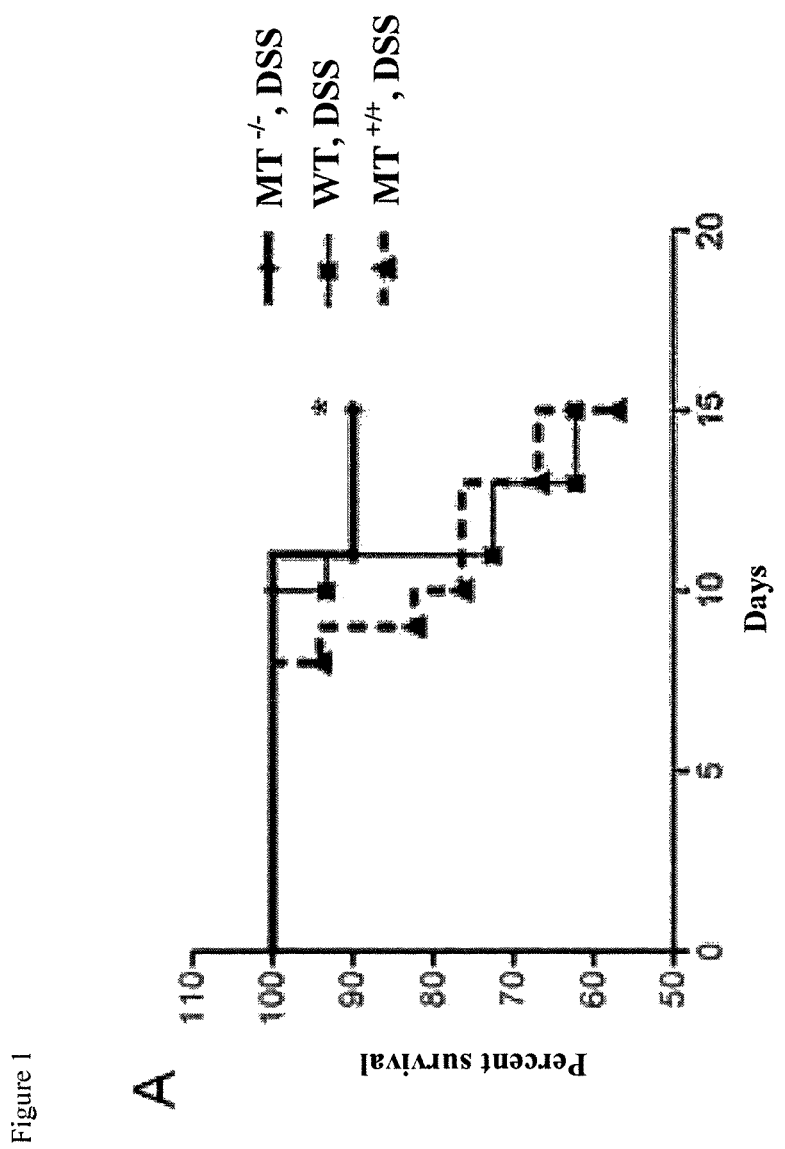
FIG. 1: Kaplan-Meier survival curve (A and C, censored data) and body weight evolution (B and D) for DSS-treated wild type (WT), MT knockout ($MT^{-/-}$) and transgenic ($MT^{+/+}$) mice and for DSS-treated UC1MT antibody and IgG1IgG11 control treated mice respectively. Body weight evolution (E) and colon length (F) for TNBS-treated control IgG1IgG11 and UC1MT treated mice compared to mice not receiving TNBS (control). A higher survival rate and less weight loss was observed for $MT^{-/-}$ mice and UC1MT antibody treated mice compared to control mice. Mice treated with the UC1MT antibody tended to lose less weight with significantly less colon shortening after TNBS treatment compared to control treated mice. Data are presented as mean±SEM. *p<0.05.
Figure 1:
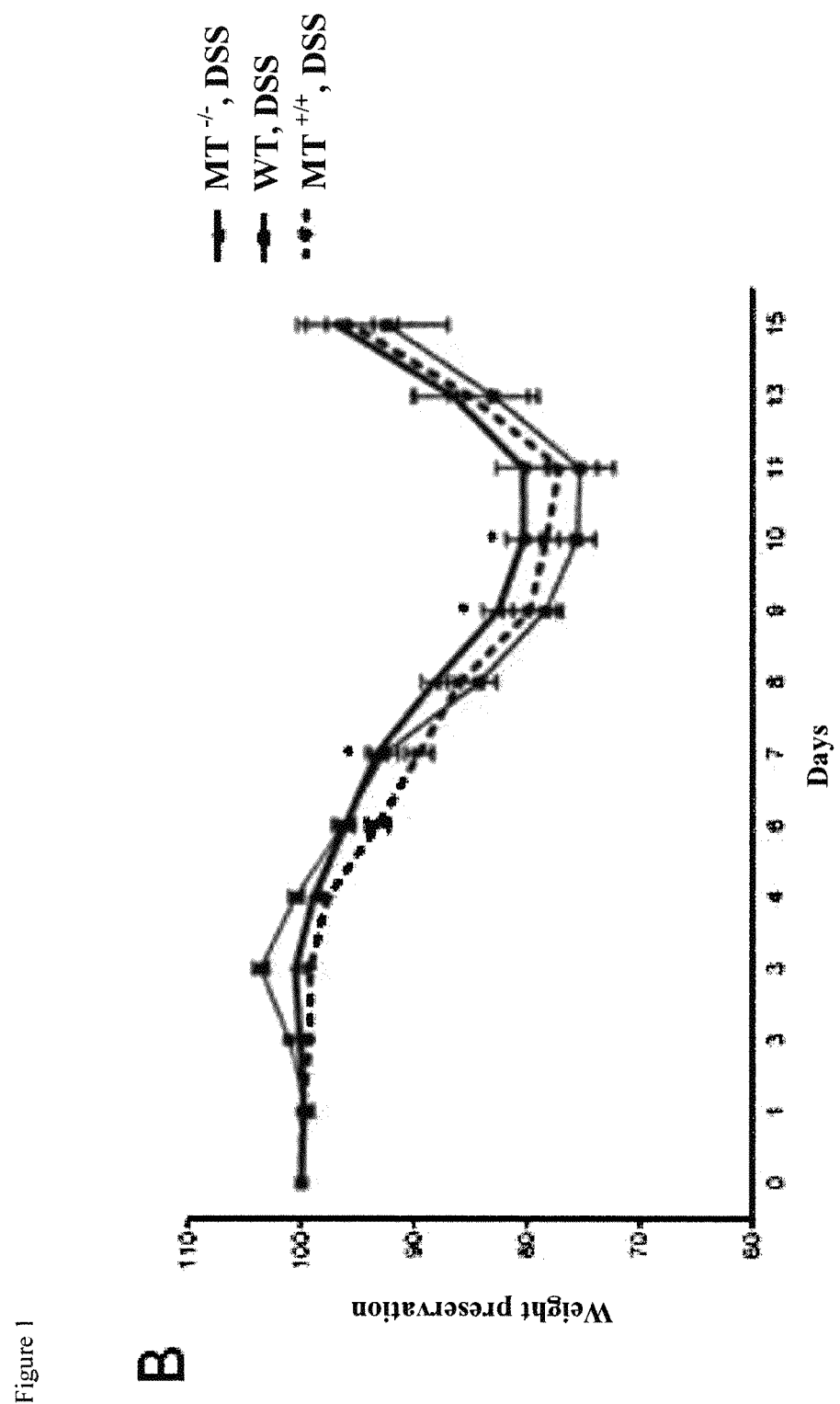
Figure 1:
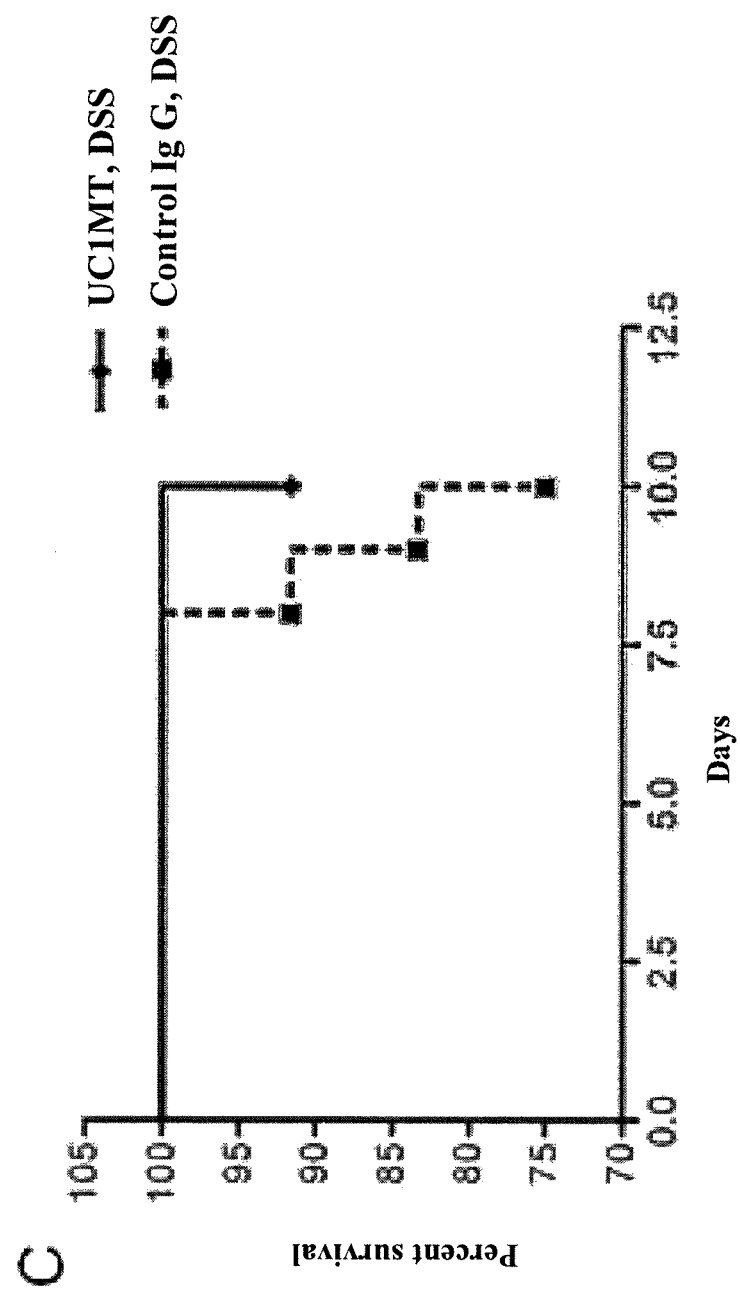
Figure 1:
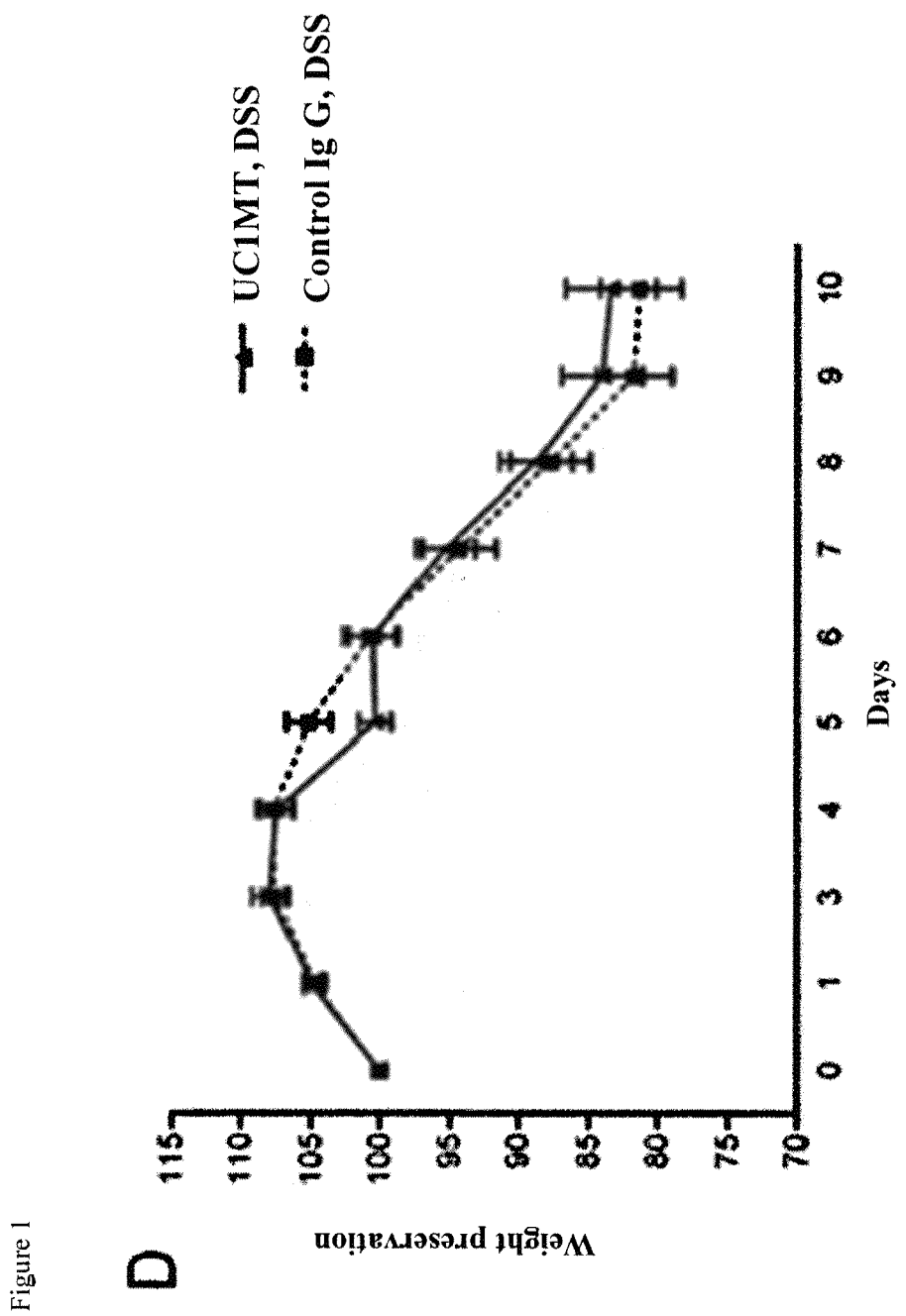
Figure 1:
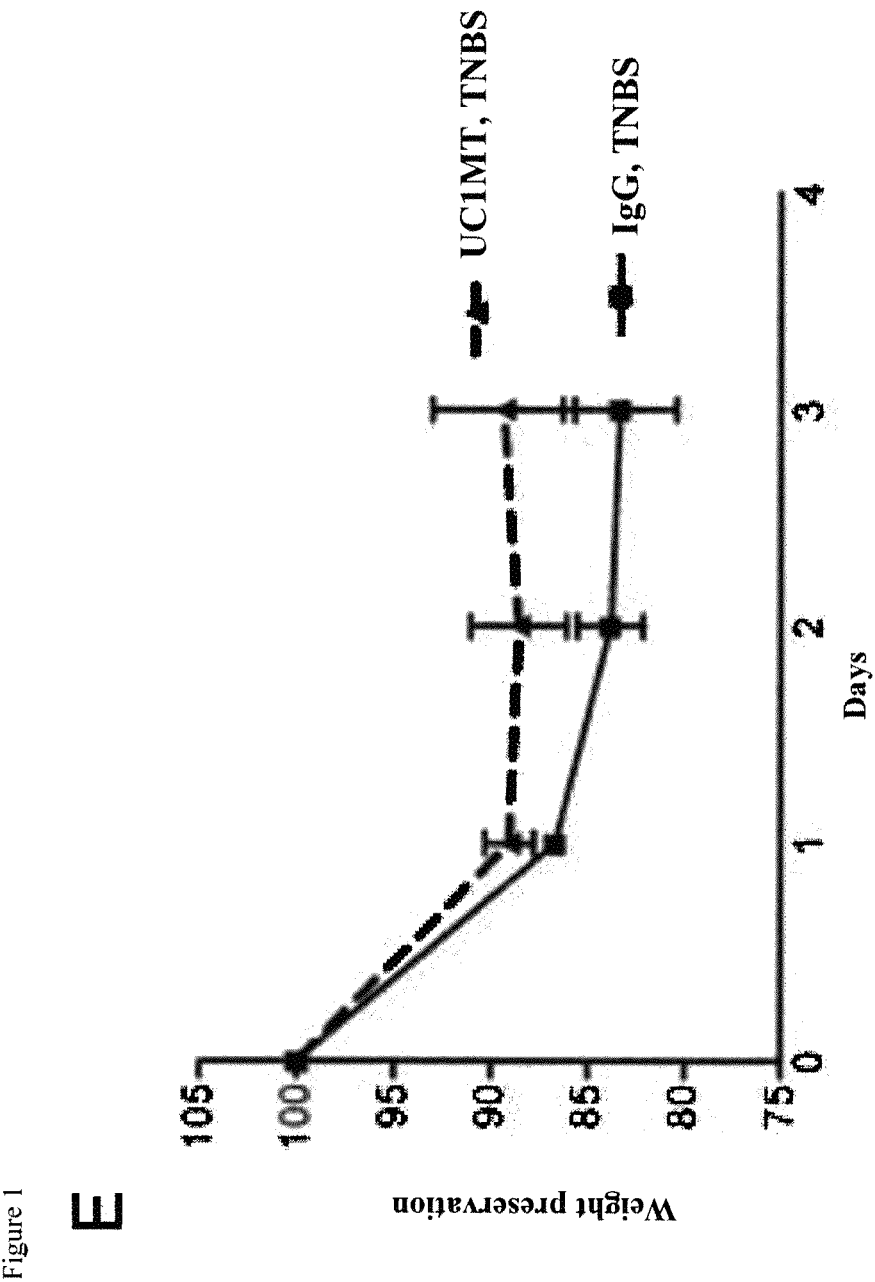
Figure 1:
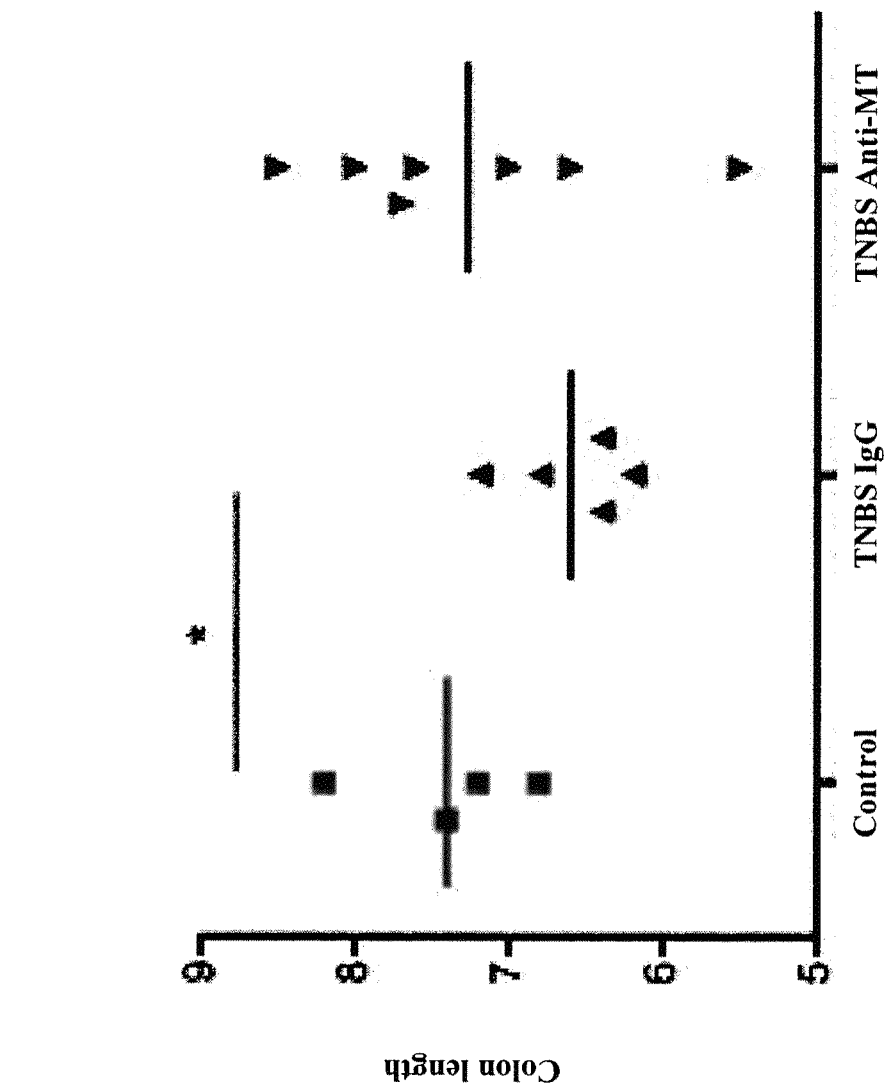

The term 'an antagonist targeting metallothionein' means an antibody which specifically or selectively binds to a metallothionein. It is further clear that the antibodies of the present invention can be prepared by any method known in the art. Examples of the latter methods are e.g. described in WO 2010/037864 and US 2003/007973.

'Metallothionein' means any of the 18 isoforms of metallothionein that have been identified in humans and are grouped as MT1 to MT4. Where MT3 and MT4 are constitutively expressed, MT1 and MT2 are highly inducible and can be secreted (Lynes et al. 2006; Laukens et al. 2009). The antibodies of the present invention specifically target or bind to the secreted metallothioneins.

'Inflammatory bowel disease', comprising Crohn's disease and ulcerative colitis, means a group of inflammatory conditions of the colon and/or the small intestine (i.e. inflammation of the intestine). The term 'intestinal inflammation' more specifically refers to Crohn's disease, ulcerative colitis, collagenous-, lymphocytic-, ischemic-, diversion- and indeterminate colitis and Behçet's disease in mammals.

The term 'antibody or a fragment thereof' relates to an antibody characterized as being specifically directed against metallothionein or any derivative thereof specifically binding to said metallothionein or an antigen-binding fragment thereof specifically binding to said metallothionein, particularly of the F(ab')2, F(ab) or single chain Fv (scFv) type, or any type of recombinant antibody thereof such as a nanobody specifically binding to said metallothionein. According to particular embodiments, the anti-metallothionein antibodies are monoclonal antibodies that selectively and preferentially bind to metallothioneins. More specifically, the present invention relates to the antibody denominated as clone 'UC1MT' as described in US 2003/0007973 and as commercially available from Abcam Inc, Cambridge, Mass. Clone UC1MT has also been described by Lynes et al. (Toxicology 1993 (85): 161-177): The monoclonal antibodies of the present invention can be further humanized or may be human monoclonal antibodies. The antibodies of the present invention can be further modified for various uses as is known in the art.

The terms 'specifically or selectively binding' to metallothionein refer to a binding reaction that is determinative of the presence of a metallothionein in a heterogeneous population of proteins and other biologics. Thus, under designated immunoassay conditions, the specified antibodies of the present invention bind to a metallothionein at least two times the background and do not substantially bind in a significant amount to other proteins than metallothioneins present in the sample. Specific binding to an antibody under such conditions may thus require an antibody that is selected for its specificity to a metallothionein.

By the term 'treatment' is meant the medical management of a patient with the intent to cure, ameliorate, stabilize, or prevent the onset of intestinal inflammation in mammals such as human patients via administering an effective amount of the antagonist/antibody of the present invention. It is further understood that appropriate doses of said compounds (which can also be denominated as drugs or pharmaceutical compositions) depends upon a number of factors within the knowledge of the ordinary skilled physician. The dose of these compounds will vary, for example, depending upon the identity, size, and condition of the patient being treated, upon the route of administration of said compounds (i.e. parenteral (intravenous, intradermal, subcutaneous), oral, transdermal, transmucosal or rectal) and upon the effect which the skilled physician desires the compound to have. A pharmaceutical composition is formulated to be compatible with its intended route of administration. Suitable diluents, solvents, antioxidants, chelating agents, buffers, carriers, isotonic agents, binding agents, adjuvants, flavoring agents, propellants, detergents and the like are described in detail in, for example, WO 03/004989.

The present invention thus relates to a method of treating or inhibiting inflammatory bowel disease or other inflammatory diseases of a patient in need thereof, comprising: administering to said patient a therapeutically-effective amount of a composition comprising an antagonist targeting metallothionein of the present invention.

The following examples are provided to better illustrate particular embodiments, and they should not be considered limiting the invention.

EXAMPLES

Animals

MT knockout ($MT^{-/-}$), transgenic ($MT^{+/+}$) and wild type (WT) mice (all C57BL/6 background) were kindly provided by Prof. Michael Lynes, University of Connecticut. C57BL/6J-Mttm1Bri Mt2tm1Bri mice were bred from C57BL/6J backcrossed to the Mt1,2 knockout construct obtained from Jackson Laboratory Stock Number 002211, strain 12957/SvEvBrd-Mt1tm1Bri Mt2tm1Bri/J as described in Crowthers et al. (2000), whereas the C57BL/6J-Tg(Mt1) mice were bred from C57BL/6J backcrossed to the Mt1 transgene obtained from Jackson Laboratory Stock Number 002209, strain Tg(Mt1)174Bri/J. Animals were housed and reared in the laboratory animal facility at the University Hospital Ghent according to the institutional animal healthcare guidelines. This study was approved by the Institutional Review Board of the Faculty of Medicine and Health Science of Ghent University (ECD 10/11).

Dextran Suphate Sodium (DSS)-Induced Colitis in WT, $MT^{-/-}$ and $MT^{+/+}$ Mice Thirty 8 to 10 week old animals of each group received 4% DSS in their drinking water for 7 days followed by 7 days of normal drinking water. Mice were matched for initial body weight prior to start of the experiment and body weight was further measured daily. Five animals of each group were anaesthetized with isoflurane in oxygen for blood sampling and sacrificed by cervical dislocation at day 0 (D0), 3 (D3), 7 (D7), 10 (D10) and 15 (D15). Serum samples were stored at −80° C. Colonic epithelial cells were isolated using the Cell Recovery Solution (BD Bioscience, Belford, Mass.) and lysed for RNA and protein extraction. Tissue samples for myeloperoxidase assay (MPO) and protein lysates were flash frozen, colon tissue for immunohistochemistry was fixed in formalin.

Treatment with the UC1MT Anti-MT Antibody or IgG1 Control During Colitis

DSS-Induced Colitis Model:

Twenty-four 8 week old C57BL/6 mice received 4% DSS in their drinking water for 7 days and were followed up for weight loss and survival until D10. Mice were randomized at D4 and treated intraperitoneally with 4 mg/kg anti-MT antibody or an equivalent volume IgG1 (control) on D4, D6 and D8. The UC1MT monoclonal anti-MT antibody was kindly provided by Prof. Michael Lynes, University of Connecticut. Samples were prelevated in the same manner as described for the former experiment.

2,4,6-trinitrobenzenesulfonic acid (TNBS)-induced colitis model:

Fifteen 8 week old WT mice were treated intrarectally with 100 µl of a 1:1 solution of absolute ethanol and 5% TNBS on D0, as described earlier. Mice were treated every day with 4 mg/kg UC1 MT antibody or an equivalent volume IgG1 (control). Four mice received 50% ethanol alone as control for the TNBS. Samples were taken at D3, as described in the DSS-induced colitis.

$MT^{-/-}$ Mice Develop a Less Severe Form of DSS Colitis

The role of MTs during intestinal inflammation was first explored using mice lacking or over-expressing MTs in DSS-induced colitis. Wild type, $MT^{-/-}$ and $MT^{+/+}$ mice were treated for 7 days with DSS, followed by 7 days of normal drinking water to evaluate both the induction and recovery from acute colitis. Data were obtained at different time points.

Most strikingly, 48% of the $MT^{+/+}$ mice died during the course of colitis, whereas this was only the case for 10% of the $MT^{-/-}$ mice ($p<0.05$, FIG. 1A). This higher survival rate was accompanied with significant less body weight loss for $MT^{-/-}$ mice at D6 and D7 compared to $MT^{+/+}$ and at D9 and D10 compared to WT mice ($p<0.05$, FIG. 1B). Moreover, $MT^{-/-}$ mice showed reduced histological inflammation and neutrophil infiltration, assessed by MPO assay ($p<0.05$ at D10, for both parameters, FIGS. 2A and B). No differences could be observed for colonic cytokine expression, mucosal macrophage infiltrate, mucosal hypoxia, vascularization or proliferation between groups.

Figure 2:
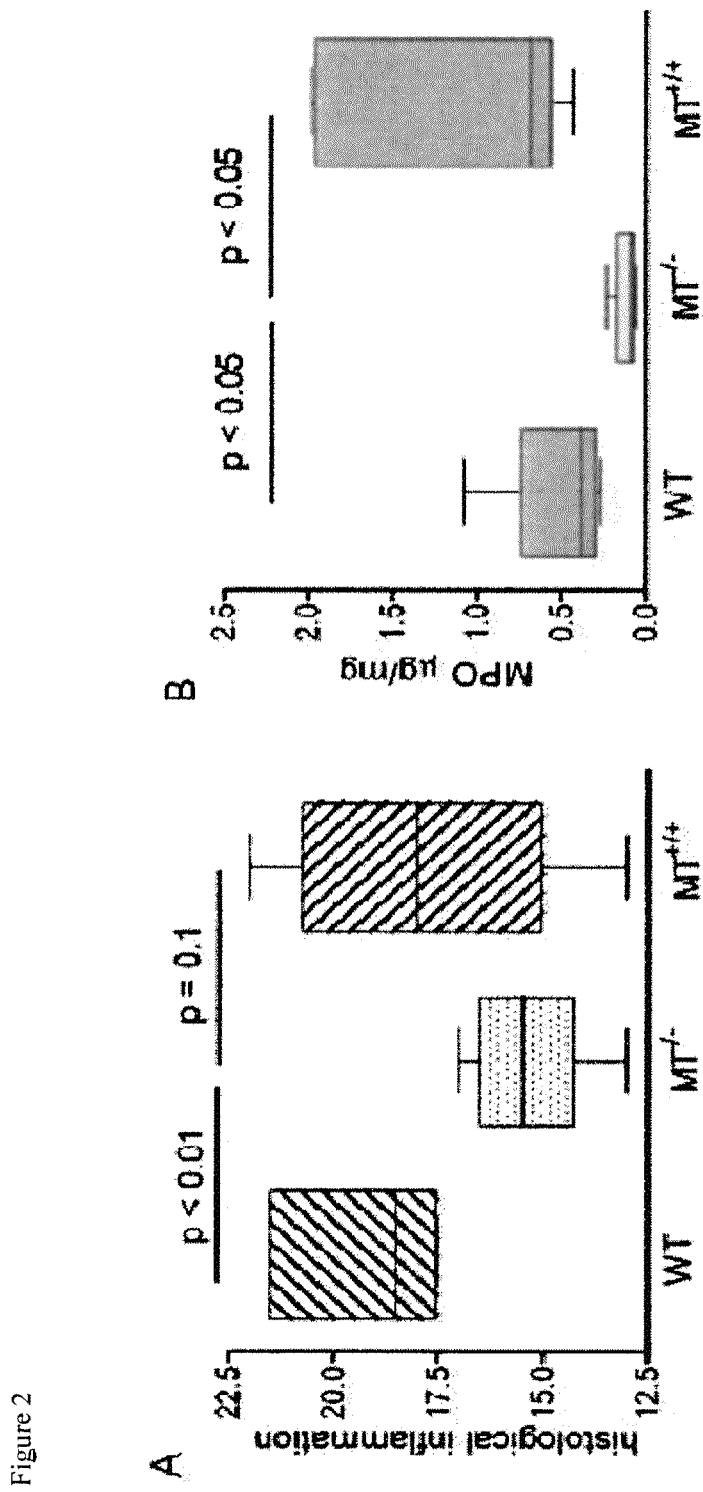
FIG. 2: Histological inflammation score (A) and myeloperoxidase activity (neutrophil infiltration) (B) for DSS-treated wild type (WT), MT knockout ($MT^{-/-}$) and MT transgenic ($MT^{+/+}$) mice at day 10. Representative pictures for macrophage infiltration (F4/80 staining) in IgG1IgG11 control and UC1MT treated mice after DSS (C) and TNBS (D) treatment. $MT^{-/-}$ mice scored significantly better for histological inflammation and neutrophil infiltration. UC1MT treated mice had significantly less macrophage infiltrate compared to IgG1IgG11 control treated mice after DSS- and TNBS-colitis induction (p<0.05). Data are presented as mean±SEM.
Figure 2:
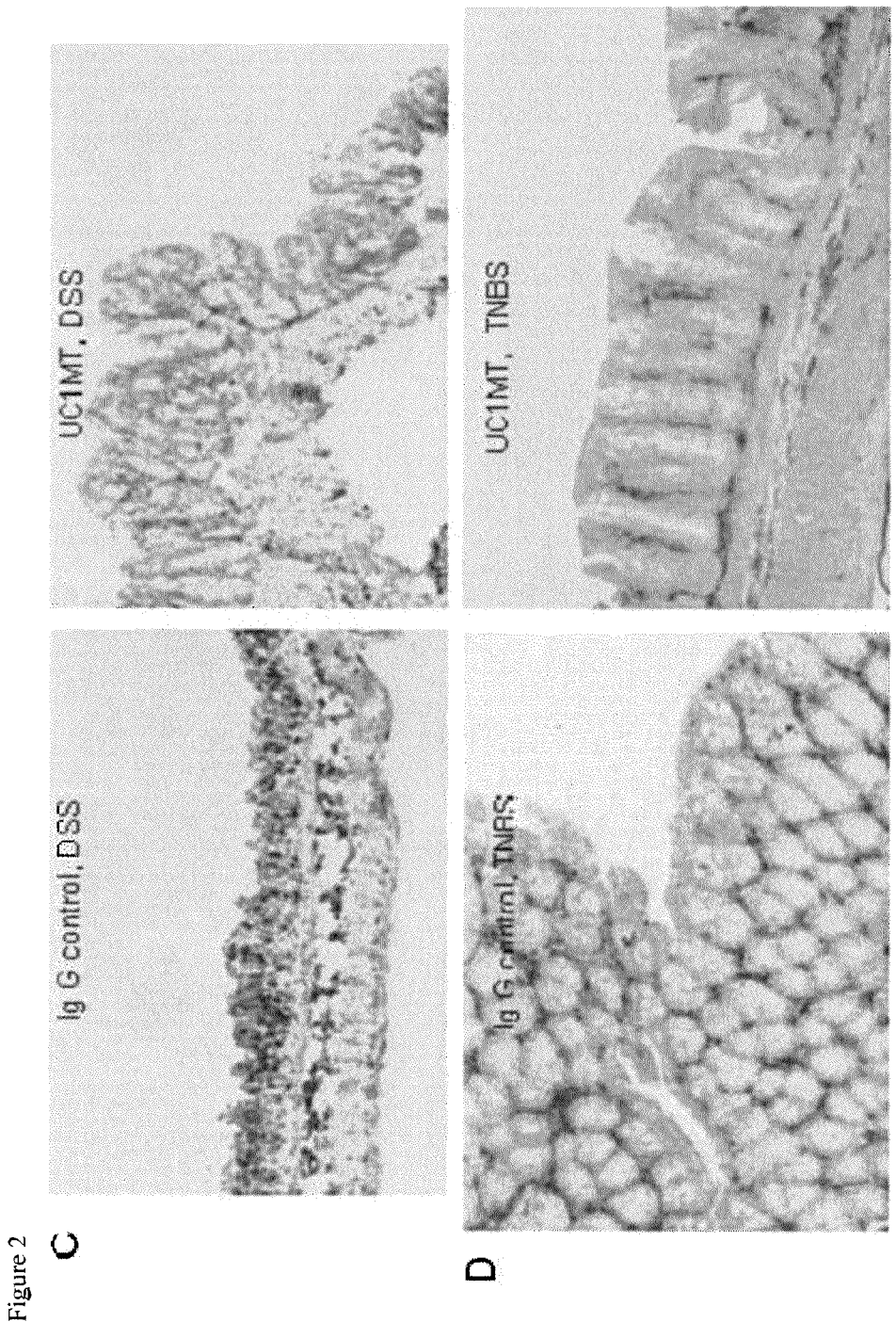

Monoclonal Anti-MT Treatment Reduces Signs of Inflammation in Experimental Colitis To further explore the observed protection in case of MT absence, the effect of targeting MTs using the monoclonal UC1MT anti-MT antibody was tested in two experimental models for acute colitis. Mice received DSS in their drinking water from D0 to D7. At D4, mice were randomized in 2 groups receiving 4 mg/kg UC1MT antibody or an isotype control at D4, 6 and 8. Mice were sacrificed for sampling at D10. Confirming the protective effect in the $MT^{-/-}$ mice, mice receiving anti-MT antibody tended to score better for weight loss and survival (FIGS. 1C and D). Significantly less inflammatory cell infiltrate was present at D10 for UC1MT treated mice and the observed infiltrate represented macrophages, as demonstrated by immunohistochemical staining for F4/80 ($p<0.05$, FIG. 2C). Finally, we evaluated the potency of the UC1MT antibody in TNBS-induced acute colitis, characterized by a transmural inflammation 4 days after intra-rectal instillation of TNBS. Anti-MT treated mice tended to lose less weight with significantly less colon shortening compared to control treated mice (FIGS. 1E and F). Complementary to the results of the DSS-experiment, UC1MT treated mice showed significant less mucosal macrophage infiltrate compared to control treated mice (FIG. 2D).

Metallothionein Acts a Potent Chemokine

Figure 3:
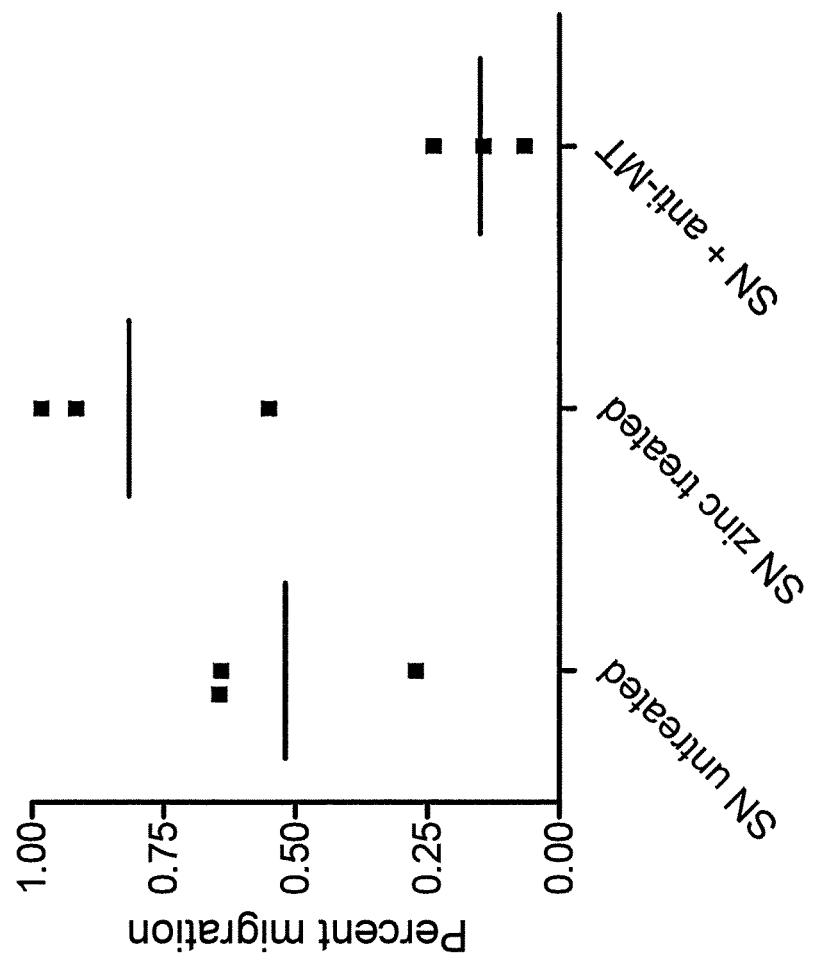
FIG. 3: Metallothioneins are secreted from intestinal epithelial cells and function as chemokines in vitro. Ficoll-isolated blood leukocyte migration towards supernatant (SN) of zinc treated (to induce MT synthesis) HT29 colonic epithelial cells in Boyden transwell chambers is higher compared to SN of untreated cells. Chemokine function is inhibited by the addition of anti-MT antibodies as shown by reduced leukocyte migration towards SN containing anti-MT antibodies.

Supernatant of zinc treated HT29 cells containing high MT levels attracts more blood leukocytes in a Boyden transwell assay than untreated cells (FIG. 3).

The UC1MT Antibody Abolishes the Chemotactic Capacity of MTs

In line with previous findings published by Yin et al, significantly less leukocyte migration could be detected using supernatant containing the UC1MT antibody compared to control supernatant (FIG. 3).

In summary, the inventors found that a lack of MTs is beneficial in experimental colitis. Moreover, treatment with an anti-MT antibody reduced the chemotactic properties of extracellular MT, resulting in reduced leukocyte infiltration and dampening of the inflammatory response during colitis that intends to avoid some or all of the negative side effects of other biologic treatments currently used for IBD Hence, anti-MT is an attractive novel biological in the treatment of IBD patients.

REFERENCES

K. Inoue, H. Takano, A. Shimada, M. Satoh, Metallothionein as an anti-inflammatory mediator, Mediators Inflamm. 2009 (2009) 101659.

Waeytens, M. De Vos, D. Laukens, Evidence for a potential role of metallothioneins in inflammatory bowel diseases, Mediators Inflamm. 2009 (2009) 729172.

C. D. Tran, J. M. Ball, S. Sundar, P. Coyle, G. S. Howarth, The role of zinc and metallothionein in the dextran sulfate sodium-induced colitis mouse model, Dig. Dis. Sci. 52 (2007) 2113-2121.

H. S. Oz, T. Chen, W. J. S. de Villiers, C. J. McClain, Metallothionein overexpression does not protect against inflammatory bowel disease in a murine colitis model, Med. Sci. Monit. 11 (2005) 69-73.

L. Devisscher, P. Hindryckx, H. Peeters, M. De Vos, D. Laukens, The hypoxia adaptive response regulates metallothionein expression in intestinal epithelial cells, Oral presentation Belgian Week of Gastroenterology 2011, Liege.

S. K. De, M T McMaster, G. K. Andrews, Endotoxin induction of murine metallothionein gene expression, J. Biol. Chem. 265 (1990) 15267-74.

D. Laukens, A. Waeytens, P. De Bleser, C. Cuvelier, M. De Vos, Human metallothionein expression under normal and pathological conditions: mechanisms of gene regulation based on in silico promoter analysis, Crit. Rev. Eukaryot Gene Expr. 19 (2009) 301-317.

M. A. Lynes, K. Zaffuto, D. W. Unfricht, G. Marusov, J. S. Samson, X. Yin, The physiological roles of extracellular metallothionein, Exp. Biol. Med. 23 (2006) 1548-1554.

X Yin, D. A. Knecht, M. A. Lynes, Metallothionein mediates leucocyte chemotaxis, BMC Immunol. 6 (2005) 21.

K. C. Crowthers, V. Kline, C. Giardina, M. A. Lynes (2000). Augmented humoral immune function in metallothionein-null mice. Toxicol Appl Pharmacol 166 (2000) 161-72.

The invention claimed is:

1. A method for reducing leukocyte infiltration in a mammal having intestinal inflammation comprising administering to said mammal a therapeutically effective amount of a composition comprising an anti-metallothionein antibody or a fragment thereof which specifically binds to human metallothionein-1 (MT1) or human metallothionine-2 (MT2).

2. The method according to claim 1, wherein the mammal has Crohn's disease or ulcerative colitis.

3. The method according to claim 1, wherein the antibody is a monoclonal antibody.

4. The method according to claim 3, wherein the monoclonal antibody is UC1MT.

5. The method according to claim 3, wherein the monoclonal antibody is humanized.

6. The method according to claim 1, wherein the mammal is a human.

* * * * *